US010839673B2

(12) United States Patent
Cullin et al.

(10) Patent No.: US 10,839,673 B2
(45) Date of Patent: Nov. 17, 2020

(54) TELECARE SYSTEM

(71) Applicant: Doro AB, Malmö (SE)

(72) Inventors: Peter Cullin, Staffanstorp (SE); Thomas Bergdahl, Bjärred (SE)

(73) Assignee: DORA AB, Malmo (SE)

( * ) Notice: Subject to any disclaimer, the term of this patent is extended or adjusted under 35 U.S.C. 154(b) by 0 days.

(21) Appl. No.: 16/310,127

(22) PCT Filed: Jun. 16, 2017

(86) PCT No.: PCT/EP2017/064823
§ 371 (c)(1),
(2) Date: Dec. 14, 2018

(87) PCT Pub. No.: WO2017/216369
PCT Pub. Date: Dec. 21, 2017

(65) Prior Publication Data
US 2019/0180600 A1    Jun. 13, 2019

(30) Foreign Application Priority Data

Jun. 16, 2016   (EP) .................................... 16174845

(51) Int. Cl.
| | |
|---|---|
| *G08B 1/08* | (2006.01) |
| *G08B 25/01* | (2006.01) |
| *G16H 80/00* | (2018.01) |
| *A61B 5/00* | (2006.01) |
| *H04M 3/51* | (2006.01) |

(Continued)

(52) U.S. Cl.
CPC .......... *G08B 25/016* (2013.01); *A61B 5/0022* (2013.01); *A61B 5/1117* (2013.01); *A61B 5/1118* (2013.01); *A61B 5/6898* (2013.01); *G08B 25/10* (2013.01); *G16H 80/00* (2018.01); *H04M 1/72541* (2013.01); *H04M 3/5116* (2013.01); *H04W 76/18* (2018.02); *G16H 40/67* (2018.01); *H04M 1/2749* (2020.01); *H04M 1/7253* (2013.01); *H04M 1/72572* (2013.01);

(Continued)

(58) Field of Classification Search
None
See application file for complete search history.

(56) References Cited

U.S. PATENT DOCUMENTS

| | | | |
|---|---|---|---|
| 2008/0248778 A1* | 10/2008 | Boss ...................... | H04M 11/04 455/404.1 |
| 2013/0082837 A1 | 4/2013 | Cosentino et al. | |
| 2014/0077956 A1 | 3/2014 | Sampath et al. | |

FOREIGN PATENT DOCUMENTS

WO    WO 2016/034681 A1    3/2016

OTHER PUBLICATIONS

International Search Report and Written Opinion for PCT/EP2017/064823 dated Aug. 31, 2017.
(Continued)

*Primary Examiner* — Adolf Dsouza
(74) *Attorney, Agent, or Firm* — Merchant & Gould P.C.

(57) ABSTRACT

A telecare system comprises a mobile terminal, which has a controller, and a telecare terminal. The controller of the mobile terminal is configured to detect a selective action by a user, attempt to communicate with the telecare terminal using short-range wireless communication in response to the detected action, and if the communication was successful, cause transmittal of an assistance request for a first telecare service and if not, cause transmittal of an assistance request for a second telecare service.

17 Claims, 8 Drawing Sheets

(51) Int. Cl.
| | |
|---|---|
| *A61B 5/11* | (2006.01) |
| *H04W 76/18* | (2018.01) |
| *H04M 1/725* | (2006.01) |
| *G08B 25/10* | (2006.01) |
| *H04W 76/50* | (2018.01) |
| *G16H 40/67* | (2018.01) |
| *H04M 1/2749* | (2020.01) |

(52) U.S. Cl.
CPC ........ *H04M 2250/02* (2013.01); *H04W 76/50* (2018.02)

(56) References Cited

OTHER PUBLICATIONS

International Preliminary Report on Patentability for PCT/EP2017/064823 dated Sep. 13, 2018.
Search Report for European Patent Application No. 16174845.4 dated Oct. 21, 2016.

\* cited by examiner

TELECARE SYSTEM

This application is a National Stage Application of PCT/EP2017/064823, filed 16 Jun. 2017, which claims the benefit of priority to European Patent Application No. 16174845.4, filed 16 Jun. 2016, which applications are incorporated herein by reference. To the extent appropriate, a claim of priority is made to each of the above disclosed applications.

TECHNICAL FIELD

The present invention generally relates to the field of telecare, and more particularly to a telecare system comprising a telecare-enabled mobile terminal and a telecare terminal.

BACKGROUND

In modern times, as our society is facing an ageing population, needs and expectations have arisen for an efficient and yet dignified manner of allowing elderly people, as well as peoples with physical, medical or mental handicaps, to remain living at their private residences or day care centers, rather than conventional caretaking institutions such as hospitals.

People in the categories above often need attendance or assistance on a frequent basis. Such attendance or assistance is typically scheduled and provided by personnel from a caregiver center, which visits the caretaker a number of times a day or week to perform housekeeping, medication or nursing services. However, the need for attendance or assistance cannot always be predicted and scheduled in advance; the caretaker may be subjected to an accident, sudden illness or another kind of situation where urgent attendance or assistance is needed. To this end, the field of telecare systems has evolved.

In recent years, mobile terminals have been introduced which are specifically adapted for use with telecare services. In the present invention, a mobile terminal and a telecare terminal are the tool used by an individual being remotely cared for. The telecare services may, for instance, involve any of the following: assistance, attendance, medical care, emergency service or rescue of the individual. It shall therefore be explicitly noticed that in the present invention, telemedicine services and/or telehealth services may be included in the notion telecare.

The present inventors have identified some drawbacks with existing telecare systems. One such identified drawback is that the systems are not sufficiently flexible for the users' needs. Furthermore, prior art solutions are generally limited to transmitting one kind of alarm, regardless of the situation of the user. It would thus be advantageous to have a system that differentiates the telecare services depending on different factors.

SUMMARY

It is an object of the teachings of this application to overcome the problems listed above by providing a telecare system comprising a mobile terminal which comprise a controller, and a telecare terminal. The controller of the mobile terminal is configured to detect a selective action by a user, attempt to communicate with the telecare terminal using short-range wireless communication in response to the detected action, and if the communication was successful, cause transmittal of an assistance request for a first telecare service and if not, cause transmittal of an assistance request for a second telecare service.

The mobile terminal may be configured to cause transmittal of the assistance request for the first telecare service by transmitting the assistance request to the telecare terminal, wherein the telecare terminal is configured to receive the assistance request and send said assistance request as data traffic to the first telecare service.

The mobile terminal may be configured to cause transmittal of the assistance request for the second telecare service by transmitting the assistance request to the second telecare service.

The telecare terminal may comprise a control unit configured to detect a selective action by a user, attempt to communicate with the mobile terminal using short-range wireless communication in response to detected action, and if the communication was successful, cause transmittal of an assistance request for a first telecare service and if not, cause transmittal of an assistance request for a second telecare service.

The telecare terminal may be configured to cause transmittal of the assistance request for the first telecare service by transmitting the assistance request to the mobile terminal, wherein the mobile terminal is configured to receive the assistance request and send said assistance request as data traffic to the first telecare service.

The telecare terminal may be configured to cause transmittal of the assistance request for the second telecare service by transmitting the assistance request to the second telecare service.

It is also an object of the teachings of this application to overcome the problems listed above by providing a method in a mobile terminal, wherein the method comprises detecting a selective action by the user, attempting to communicate with a telecare terminal using short-range wireless communication, and if the communication was successful, causing transmittal of an assistance request for a first telecare service, and if not, causing transmittal of an assistance request for a second telecare service.

Yet another object of the teachings of this application is to overcome the problems listed above by providing a mobile terminal comprising a controller, wherein the controller is configured to perform the method in a mobile terminal such as above.

Other features and advantages of the disclosed embodiments will appear from the following detailed disclosure, from the attached dependent claims as well as from the drawings.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of the element, device, component, means, step, etc., unless explicitly stated otherwise. The steps of any method disclosed herein do not have to be performed in the exact order disclosed, unless explicitly stated.

BRIEF DESCRIPTION OF THE DRAWINGS

Objects, features and advantages of embodiments of the invention will appear from the following detailed description, reference being made to the accompanying drawings, in which.

DETAILED DESCRIPTION

Figure 1:
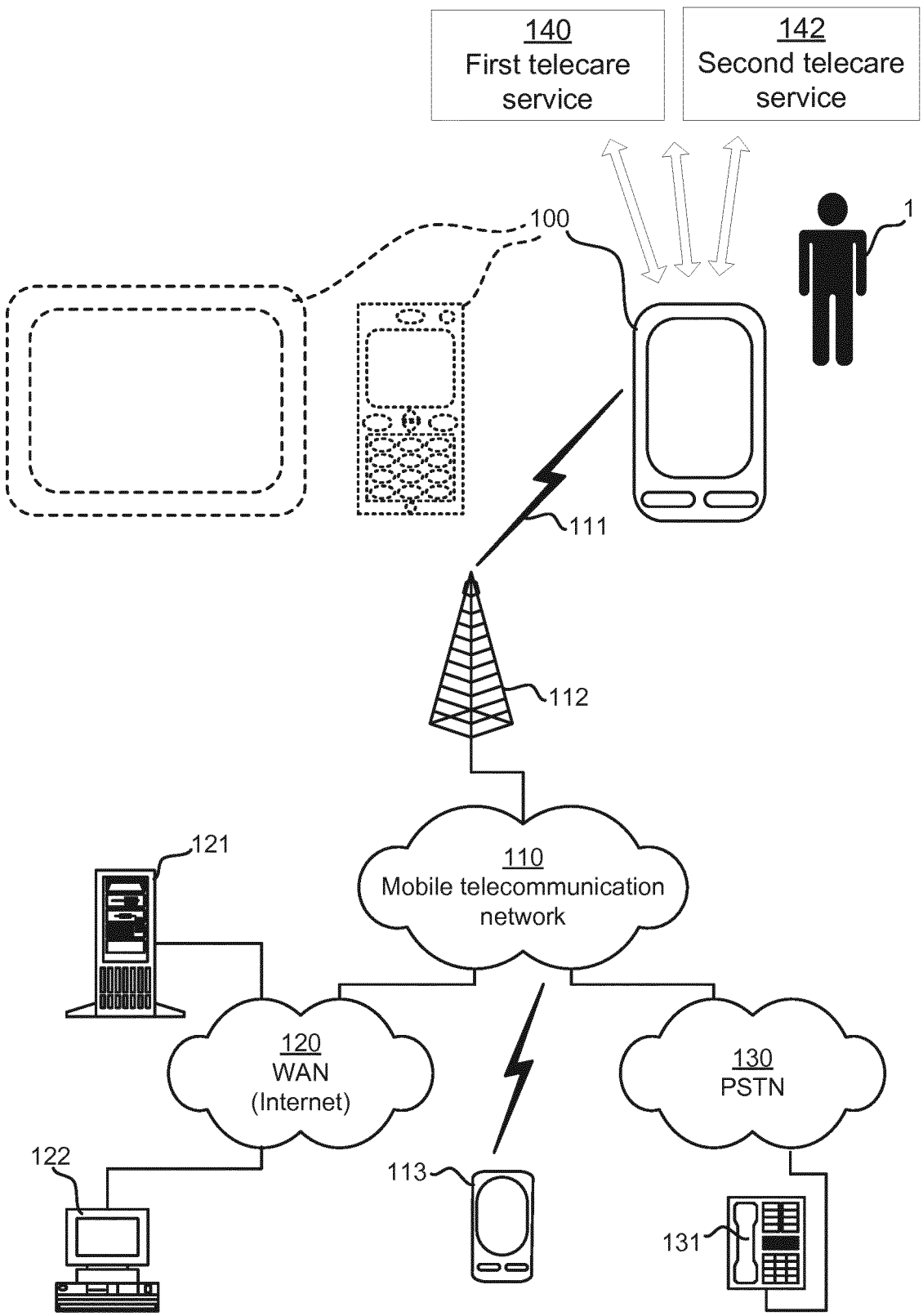
FIG. 1 is a schematic illustration of a non-limiting example of a telecommunication system in which a telecare-enable mobile terminal of the present invention may be operated.

Embodiments of the invention will now be described with reference to the accompanying drawings. The invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the particular embodiments illustrated in the accompanying drawings is not intended to be limiting of the invention. In the drawings, like numbers refer to like elements.

The telecare system enclosed herein comprises a portable electronic device, such as a mobile terminal 100, and an external device such as a telecare terminal 200. The system aims at differentiate between alarm events depending on where and/or how an alarm event was initiated.

Before turning to a detailed description of the disclosed embodiments, an exemplifying environment of the portable electronic device will be briefly described with reference to FIGS. 1 and 2 and an exemplifying environment of the external device will be briefly described with reference to FIG. 3a-b.

In FIG. 1, a portable electronic device in the form of a mobile terminal 100 is part of a cellular telecommunication system. The mobile terminal 100 may connect to a mobile telecommunication network 110 over a radio link 111 and a base station 112. The mobile terminal 100 and the mobile telecommunication network 110 may comply with any commercially available mobile telecommunication standard, for instance (without limitation) GSM, UMTS, LTE, LTE Advanced, D-AMPS, CDMA2000, FOMA and TD-SCDMA. Embodiments of the mobile terminal 100 will be described in more detail with reference to the following drawings.

A public switched telephone network (PSTN) 130 is connected to the mobile telecommunication network 110. Telephone terminals of PSTN subscribers may connect to the PSTN 130. In FIG. 1, a stationary telephone 131 is indicated as a mere example of this.

The mobile telecommunication network 110 is operatively associated with a wide area data network 120, which may be the Internet or a part thereof. Server computers 121 and client computers 122 may be connected to the wide area data network 120 to allow communication with the mobile terminal 100. The mobile terminal 100 may also communicate with other mobile terminals 113 over the mobile telecommunication network 110.

A user 1 of the mobile terminal 100 may use different mobile services, such as voice calls, Internet browsing, video calls, data calls, facsimile transmissions, still image transmissions, video transmissions, electronic messaging, multimedia streaming, gaming, and e-commerce. The invention is however not limited to any particular set of services, except telecare services which are central to the inventive aspect of the telecare system. The following description will focus on two different telecare services; a first telecare service 140 and a second telecare service 142 which is contactable by the telecare system. When providing the telecare services, the first 140 and/or the second 142 telecare service and its personnel may use devices like any of the aforementioned ones which are indicated at 113, 121, 122 and 131 in FIG. 1.

The mobile terminal 100 is not limited to any particular kind when it comes to physical design. It may, for instance, be of a well-known kind which comprises a touch-sensitive display being the primary input device as well as the primary output device for interaction with the user 1. Such mobile terminals are often referred to as smartphones. The mobile terminal 100 shown with solid lines in the uppermost part of FIG. 1 is illustrated as a smart phone.

Alternatively, the mobile terminal 100 may for instance be a tablet computer or a so called "feature phone", as illustrated with broken lines in the uppermost part of FIG. 1. As is well known, a feature phone normally includes a keypad (such as an ITU-T or PIN type keypad, having keys representing digits "0" through "9" as well as signs "*" and "#", and operation keys such as a YES/OK/CALL key and a NO/CANCEL/-HANGUP key) as the primary input device for interaction with the user 1, and a display (such as a non-touch display or a touch-sensitive display) as the primary output device for interaction with the user 1. Feature phones may consist of a single housing (the type sometimes being referred to as monoblock), or they may have two main housing parts hinged together to form a clamshell phone or a swivel phone.

The mobile terminal 100 may have various other elements, such as microphone, loudspeaker, camera, power switch, battery, charger interface, accessory interface, volume controls, and antenna. Such elements are utterly well known to the skilled person and do not require any specific description.

Figure 2:
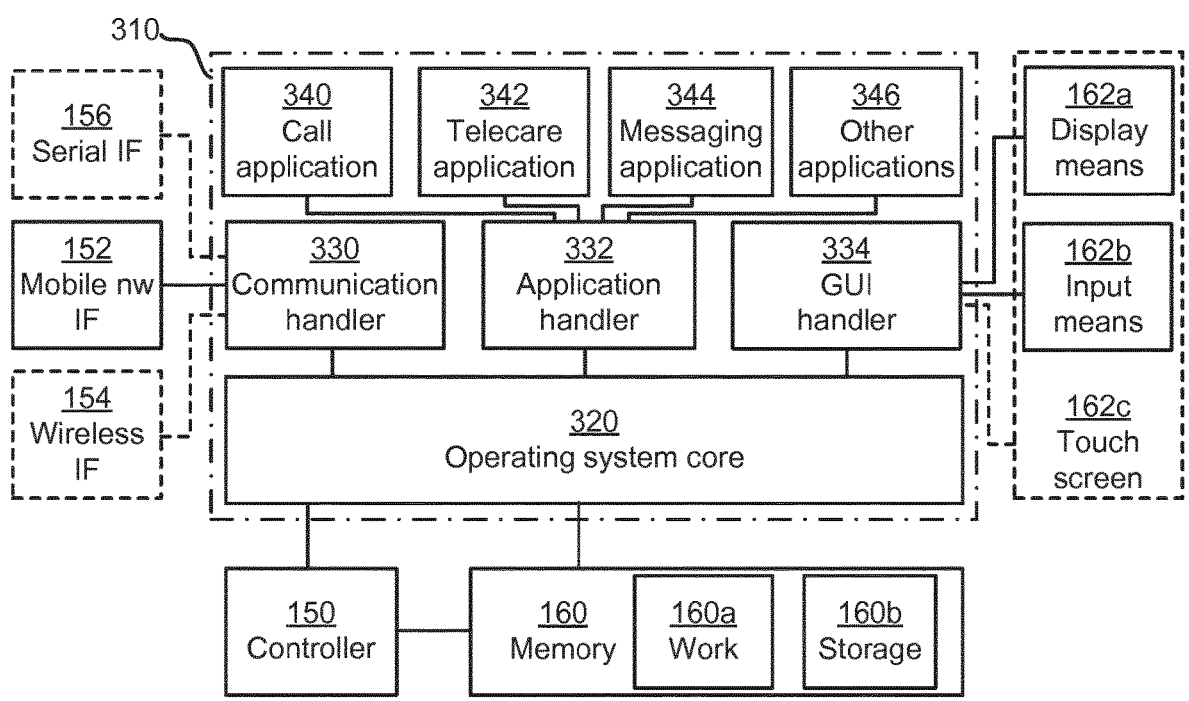
FIG. 2 is a schematic block diagram illustrating the basic internal hardware and software layout of the mobile terminal shown in FIG. 1.

Reference is now made to FIG. 2 for a description of the internal software and hardware structure of the mobile terminal 100. Software components are indicated within a dash-dotted frame 310, whereas hardware components are outside of this frame. The mobile terminal 100 has the aforementioned controller 150, being responsible for general device operations. Any commercially available central processing unit (CPU) or digital signal processor (DSP), or other programmable electronic logic device such as an application-specific integrated circuit (ASIC) or field-programmable gate array (FPGA), may be used to implement the controller 150. The controller 150 has the aforementioned associated memory 160 which includes a work memory (RAM) 160a and a non-volatile storage memory 160b, for instance in the form of EEPROM, flash memory (e.g. memory card), hard disk, or any combination thereof. The controller 150 uses the memory 160 for different purposes, for instance for storing file objects as well as data and program instructions for the software in the mobile terminal 100.

The software includes an operating system core 320 on a lower level, application programs 340-346 on an upper level for interaction with the user 1, and drivers and handlers for the hardware and the application programs on an intermediate level. The intermediate level includes a GUI handler 334 which forms the user interface towards the user 1 by controlling the display 162a and the input means 162b, as well as other I/O devices which may be included in the mobile terminal 100 (e.g. microphone, loudspeaker, vibrator, ringtone generator, LED status indicator, audio volume controls, dedicated assistance button, etc). When the display 162a is a touch-sensitive display 162c, the GUI handler 334 controls the touch-sensitive display 162c to act both as a display means and as an input means.

An application handler 332 controls the application programs 340-346, which may include a call handling (e.g. voice calls, video calls) application 340, a telecare application 342, a messaging (e.g. SMS, MMS, email, chat) application 344, as well as various other applications 346, such as applications for calendar, contacts, web browser, file handling, a control panel or settings application, a camera application, one or more video games, a word processing application, a spreadsheet application, a drawing application, a slideshow presentation application, a multimedia streaming application, etc.

In addition, the mobile terminal 100 may have a wireless interface 154 which may be adapted for communication in accordance with one or more short-range wireless communication standards such as Bluetooth, WiFi (e.g. IEEE 802.11, wireless LAN), Near Field Communication (NFC), or Infrared Data Association (IrDA). A serial interface 156, such as USB, may also be provided to allow the mobile terminal 100 to communicate over a serial cable with for instance a personal computer. Such interfaces 154, 156 may be absent in some embodiments.

The software also includes various modules, protocol stacks, drivers, etc., which are commonly designated as communication handler 330 and which provide communication support for the mobile network interface and, when applicable, the wireless interface 154 and/or the cellular interface 156.

The telecare functionality may be implemented by the telecare application 342. In addition, applications other than the telecare application 342, such as the messaging application 344 and the call handling application 340, may implement parts of the telecare functionality of the mobile terminal 100. In some embodiments, no separate application is provided to implement the telecare functionality of the mobile terminal 100; in such a case the telecare functionality may be implemented entirely by functions within the applications 340-346.

When the controller 150, for instance running the telecare application 342, of the mobile terminal 100 has detected that the user 1 has made the selective action in the user interface of the mobile terminal (e.g. actuation of the dedicated assistance button), it may in response enter an assistance request mode. While in assistance request mode the controller 150 of the mobile terminal 100 will generate an assistance request and causing transmittal of the assistance request to a telecare service 140, 142. The assistance request as well as the telecare services 140, 142 will be described more in detail with reference to FIG. 4a to 4f.

Telecare Terminal

As already mentioned, the telecare system further comprises an external device, which will now be briefly described with reference to FIG. 3a-b.

Figure 3A:
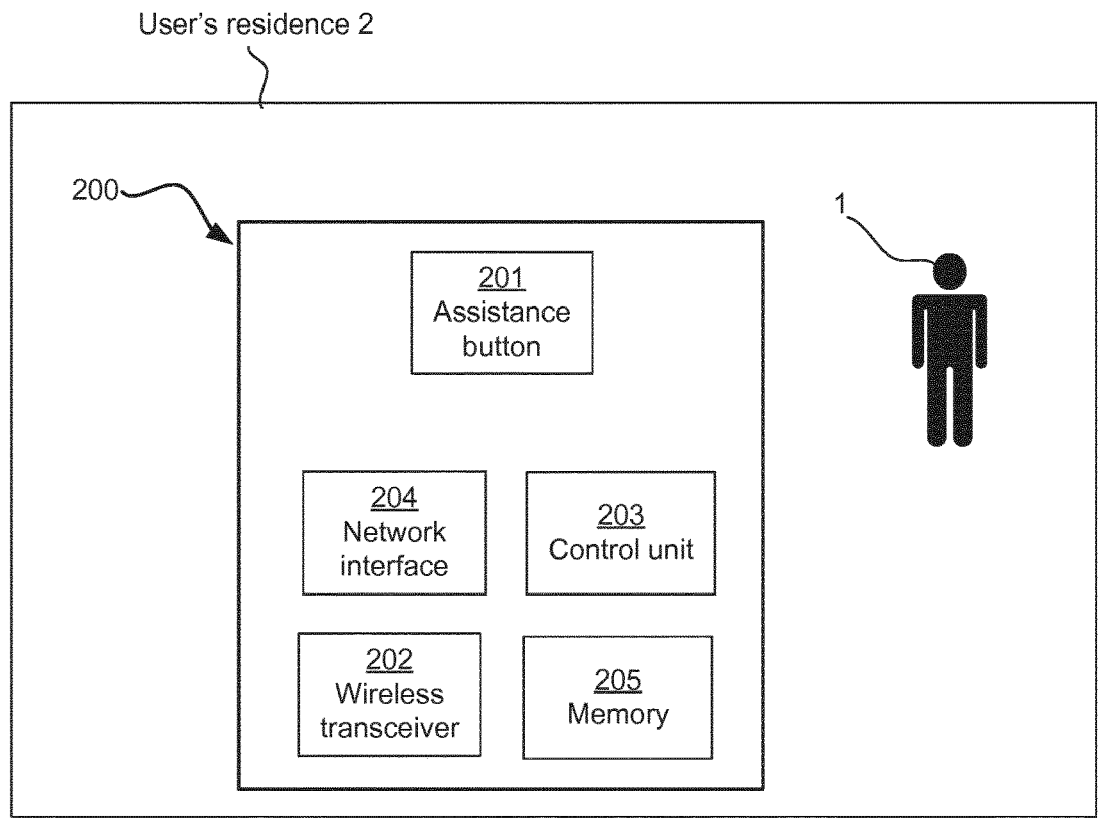
FIGS. 3a-b are schematic block views illustrating the basic internal hardware and software layout of two different embodiments of a telecare terminal.

FIG. 3a shows an external device in the form of a telecare terminal 200 which is to be arranged in a residence 2 of a user 1. The telecare terminal 200 may be configured for generating and transmitting an assistance request to a telecare service 140, 142 or to a mobile terminal 100 upon occurrence of an alarm event at the users residence 2 in which the telecare terminal 200 is installed. The alarm event, or selective action by the user 1, at the users residence 2 may for instance occur because of manual actuation of an alarm function of the telecare terminal 200. This may involve pressing an alarm button 201 on the telecare terminal. When an assistance button 201 is pressed, the user has indicated that she is in need for assistance or attendance.

The assistance button 201 may take the form of a physical mechanical button. It may also take the form of a virtual button in a graphical user interface on a touch sensitive display (not shown) of the telecare terminal 200.

The telecare terminal 200 is not limited to any particular kind when it comes to physical design. It may, for instance, also take the form of a stationary telephone device which is connected via a communications channel 102 to a first telecare service 140 (see FIG. 4a-f) or take the form of a mobile phone, such as a smartphone. The communications channel 102 may typically involve a short-range wireless data communication, but may also involve Public Switched Telephone Network (PSTN), a mobile telecommunication network (e.g. GSM, UMTS, LTE) or a wide area network (WAN) (e.g. a broadband IP network), or combinations thereof.

The telecare terminal 200 as shown in FIG. 3a has a network interface 204 for connecting to one or more communications network(s). The network interface 204 may comply with any commercially available mobile telecommunications standard, including but not limited to GSM, UMTS, LTE, D-AMPS, CDMA2000, FOMA and TD-SCDMA. Alternatively or additionally, the network interface 204 may comply with one or more short-range wireless data communication standards such as Bluetooth®, WiFi (e.g. IEEE 802.11, wireless LAN), Near Field Communication (NFC), RF-ID (Radio Frequency Identification) or Infrared Data Association (IrDA).

Further, the telecare terminal 200 may have a wireless transceiver 202 for interaction with the mobile terminal 100. In an advantageous embodiment, the wireless transceiver 202 is capable of short-range wireless data communication such as, for instance, Bluetooth®, WLAN/WiFi, NFC (Near Field Communication), RF-ID (Radio Frequency Identification) or IrDA (Infrared Data Association).

The telecare terminal 200 as shown in FIG. 3a has a control unit 103 being responsible for general device operations. Any commercially available central processing unit (CPU) or digital signal processor (DSP), or other programmable electronic logic device such as an application-specific integrated circuit (ASIC) or field-programmable gate array (FPGA), may be used to implement the controller 150.

Additionally, the telecare terminal 200 has a memory 205 which is operatively connected to the control unit 103. The memory 205 may be implemented by any known memory technology, including but not limited to E(E)PROM, S(D) RAM and flash memory, and it may also include secondary storage such as a magnetic or optical disc. Physically, the memory 205 may consist of one unit or a plurality of units which together constitute the memory 205 on a logical level. In some embodiments, it may be implemented at least partly by a storage area in another component of the telecare terminal 200, such as the control unit 205 and/or the wireless transceiver 202.

The telecare terminal 200 may also has a user interface, which may include a display and a set of keys or other input device, as well as other known user interface elements like a speaker and a microphone. The telecare service 140, 142 may control the operation of, and exchange data with, the telecare terminal 200 over the user interface.

Figure 3B:
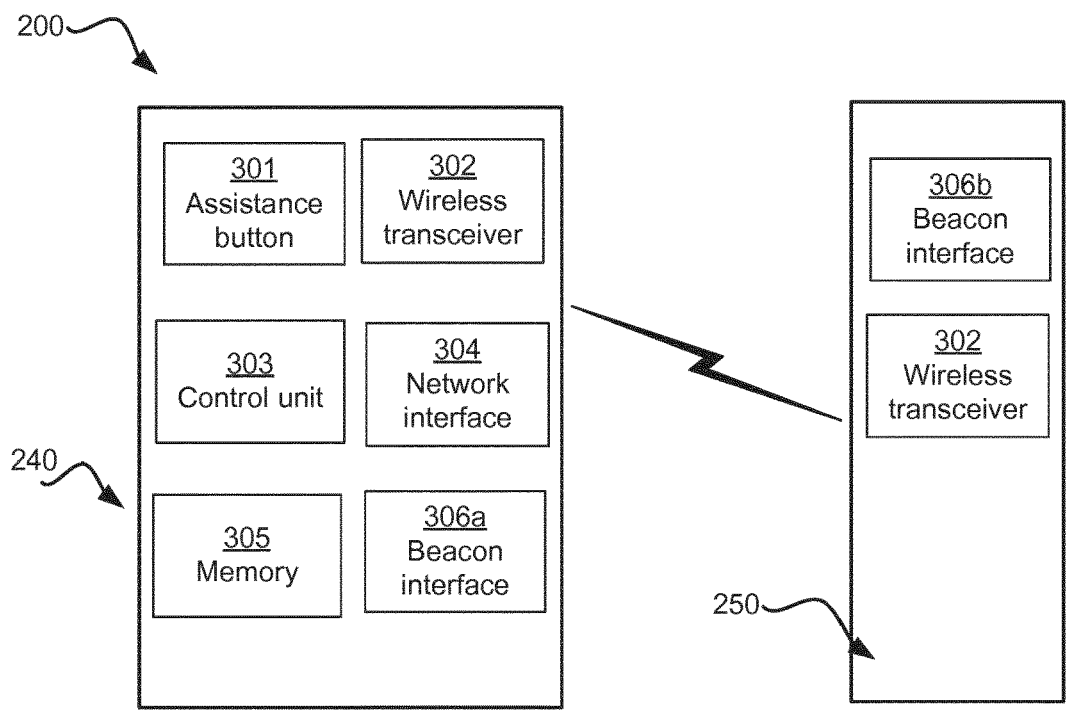

In one embodiment, as shown in FIG. 3b, the telecare terminal 200 comprises two different units, namely an assistance unit 240 and a signaling unit 250. The assistance unit 240 comprises an assistance button 301, a wireless transceiver 302, a control unit 303, a network interface 304 and a memory 305 similar to that described in reference to FIG. 3a. The assistance unit further comprises a beacon interface 306a. The signaling unit 250 comprises a wireless transceiver 302 to be able to communicate with the mobile terminal 100. In addition thereto, the signaling unit 250 comprises a beacon interface 306b, which allows for interactions with the assistance unit 240.

Furthermore in one embodiment, the telecare terminal 200 may be supplemented by a portable unit (not shown), such as a wrist belt device carried around the caretaker's 1 wrist. Such a wrist belt device typically has an alarm button and wireless communication means for transmitting a local alarm signal to the telecare terminal 200, which as a result generates and causes the assistant request to be transmitted to the telecare service 140, 142.

EXAMPLES

The provision of a telecare system comprising a mobile terminal 100 and a telecare terminal 200 which differentiates between different telecare services will solve or at least reduce the problems discussed above with reference to a prior art telecare system. This is done by the fact that the mobile terminal 100 and the telecare terminal 200 in the telecare system interacts wirelessly with each other, and a generated assistance request is then sent to a first telecare service 140 or a second telecare service 142 depending on the short-range wireless interaction. A telecare service may comprise a center of telecare advisors or other personnel working at the telecare center, which gives advice regarding health-related questions. A telecare service may send assistance, send medical care, and send an emergency or rescue action to relieve the user in a critical situation The first telecare service 140 may be in contact with the user when the user is in her residence, possibly by initiating an alarm on the telecare terminal 200 or at her mobile terminal 100. The first telecare service 140 may thus relate to a service that is coupled to the home environment, such as being connected to a neighbor, a local nursing home or to a local health center.

The second telecare service 142 may be in contact with the user when the user is not at her residence, possibly by initiating an alarm on her mobile terminal 100. The second telecare service 142 may thus relate to a service that is not bound to the location of the user, such as a relative or a third party service provider.

The possible differences between the first and second telecare services 140, 142 and other benefits with the system will become more apparent from the remainder of this detailed description.

The communication between the mobile terminal 100 and the telecare terminal 200 and in turn the communication with the first telecare service 140 and/or the second telecare service 142 will now be described further with exemplified embodiments with reference to FIG. 4a-f.

Figure 4A:
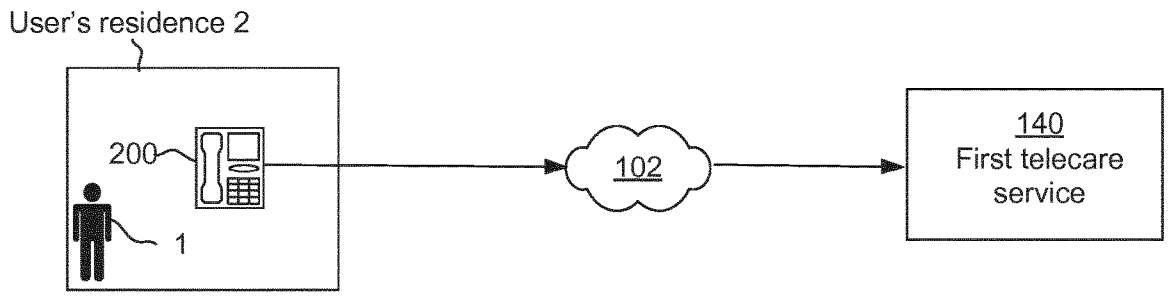
FIGS. 4a-f are schematic illustrations of non-limiting examples of the mobile terminal and the telecare terminal.
Figure 4B:
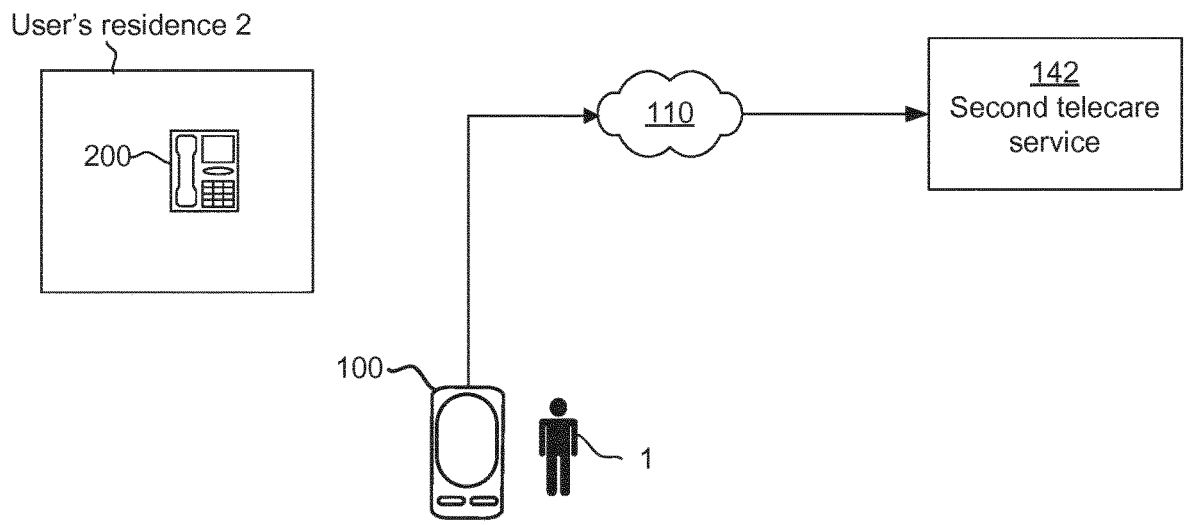
Figure 4C:
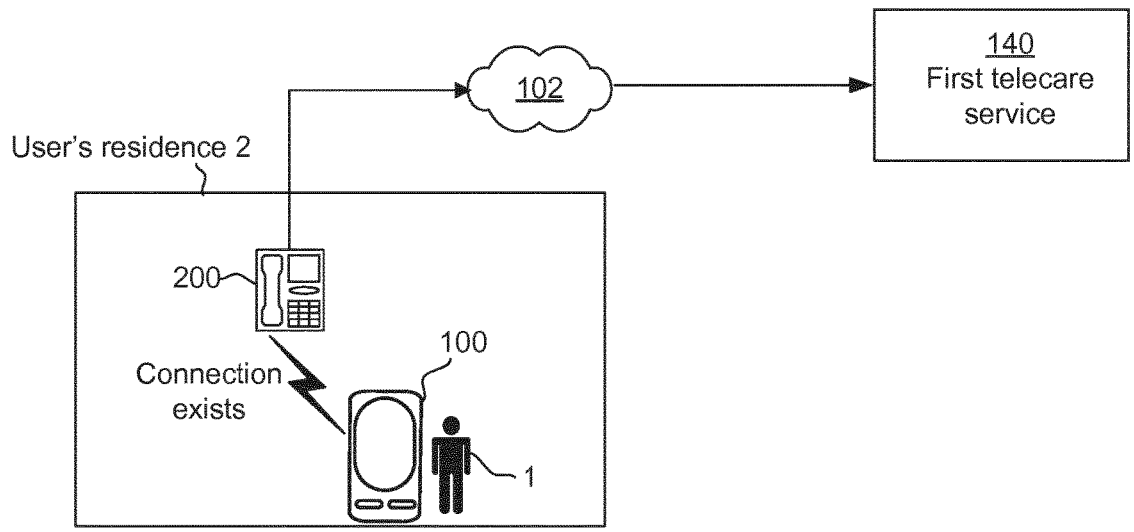

FIG. 4a-c show examples of an embodiment in a situation where the user 1 has indicated assistance by using her mobile terminal 100 or by using the telecare terminal 200.

In the embodiment as seen in FIG. 4a, a telecare terminal 200 is arranged in or in the vicinity of the residence 2 of the user 1. When the user 1 finds herself in need of assistance, she may request for assistance by a selective action in the telecare terminal 200. The selective action may typically be actuation of a dedicated assistance button 201 being part of the telecare terminal 200.

The control unit 203 of the telecare terminal 200 will generate an assistance request in response to the detected action. The assistance request may be sent through a communication channel 102, for example as data traffic, to a first telecare service 140.

In FIG. 4b, the telecare terminal 200 is arranged inside the residence 2 of the user while the user 1 and her mobile terminal 100 are arranged at a distance outside from the residence 2 of the user. When the controller 150 (for instance running the telecare application 342) of the mobile terminal 100 has detected that the user 1 has made the selective action in the user interface of the mobile terminal (e.g. actuation of the dedicated assistance button), it may in response enter an assistance request mode. While in assistance request mode the controller 150 of the mobile terminal 100 will generate an assistance request and attempt to establish a wireless connection between the mobile terminal 100 and the telecare terminal 200. The wireless connection may be a short-range wireless data communication, such as, for instance, Bluetooth, WLAN/WiFi, NFC, RF-ID or IrDA.

An establishment of a short-range wireless data communication will only be successful if the mobile terminal 100 and the telecare terminal 200 are in the vicinity of each other, for example if both devices are located in the users residence 2, as seen in FIG. 4c. It is thus possible to establish if the mobile terminal 100, and thus the user 1 of the mobile terminal 100, is located in an area close to the telecare terminal 200. Hence, if the mobile terminal 100 succeeds in establishing a short-range wireless data communication with the telecare terminal 200, one can assume that the user 1 of the mobile terminal 100 is in the vicinity of the telecare terminal 200 and thus in the vicinity of the users residence 2. Hence, the communication is only successful if the mobile terminal 100 is within operative range of the short-range wireless communication of the telecare terminal 200. As soon will be discussed more in detail, it is beneficial to separate these two events since different telecare service actions may be needed depending on the location of the user 1 in distress.

Since the mobile terminal 100 and the telecare terminal 200 are located far from each other in the example of FIG. 4b, no short-range wireless data connection can be made. In response to the failed connection, the controller 150 of the mobile terminal 100 will cause transmittal of the generated assistance request for a second telecare service 142. The transmittal is caused by transmitting the assistance request to the second telecare service 142 through a mobile communication network 110. In some embodiments, the transmittal of the assistance request for the second telecare service 142 is caused by directly transmitting the assistance request to the second telecare service 142, hence the transmittal is transmitted by the mobile terminal 100.

It is worth mentioning that if no short-range wireless data connection can be established, the generated assistance request will still be sent without any other input from the user. As will be described more herein, the effect of not being able to establish a short-range wireless data connection is that the mobile terminal 100 will cause transmittal of the generated assistance request for a second telecare service 142 and possibly, in some embodiments, that the location where the assistance request is transmitted from (mobile terminal 100 and/or telecare terminal 200) is changed.

In the example shown in FIG. 4*c*, the telecare terminal 200, the user 1 and her mobile terminal 100 are all located in or in the vicinity of the residence 2 of the user 1. When the user 1 actuates the dedicated assistance button in the user interface of the mobile terminal 100, the mobile terminal 100 attempts to establish a short-range wireless connection between the mobile terminal 100 and the telecare terminal 200. If the mobile terminal 100 succeeds in establishing a short-range wireless data communication with the telecare terminal 200, the controller 150 generates an assistance request and causes transmittal of the assistance request for a first telecare service 140. The controller 150 transmits the assistance request to the telecare terminal 200, thereby enabling the telecare terminal 200 to receive the assistance request and send the assistance request through a communication channel 102, for example as data traffic, to a first telecare service 140.

Figure 4D:
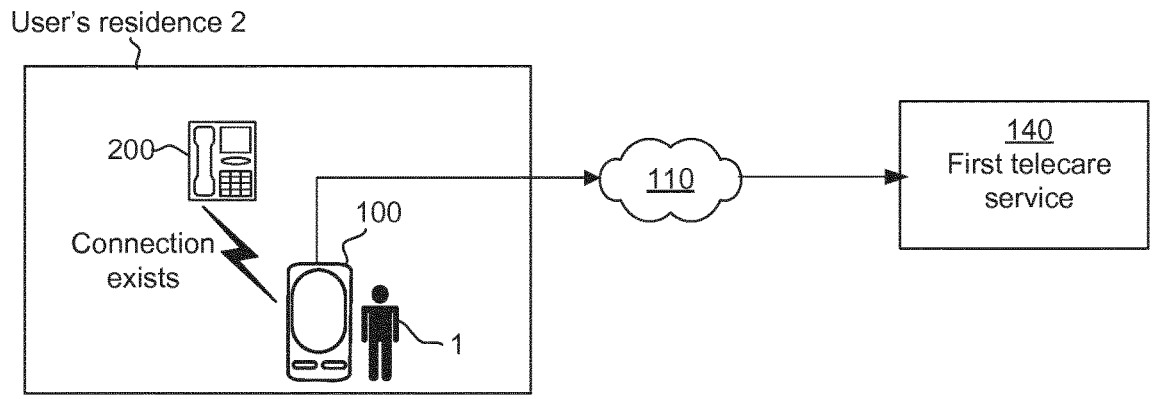

Another embodiment is shown in FIG. 4*d*, where the telecare terminal 200, the user 1 and her mobile terminal 100 all are located in the residence 2 of the user. Once the user has made the selective action in the user interface of the mobile terminal (e.g. actuation of the dedicated assistance button) the controller 150 of the mobile terminal 100 will attempt to establish a wireless connection between the mobile terminal 100 and the telecare terminal 200. If the attempt succeeds and a wireless communication is established, the generated assistance request is sent from the mobile terminal 100 to the first telecare service through a mobile communication network 110. Hence, the difference between this embodiment and the one presented with reference to FIG. 4*c* is that here the mobile terminal 100 will communicate directly to the first telecare service 140, and not via the telecare terminal 200, once a short-range wireless connection is established.

Figure 4E:
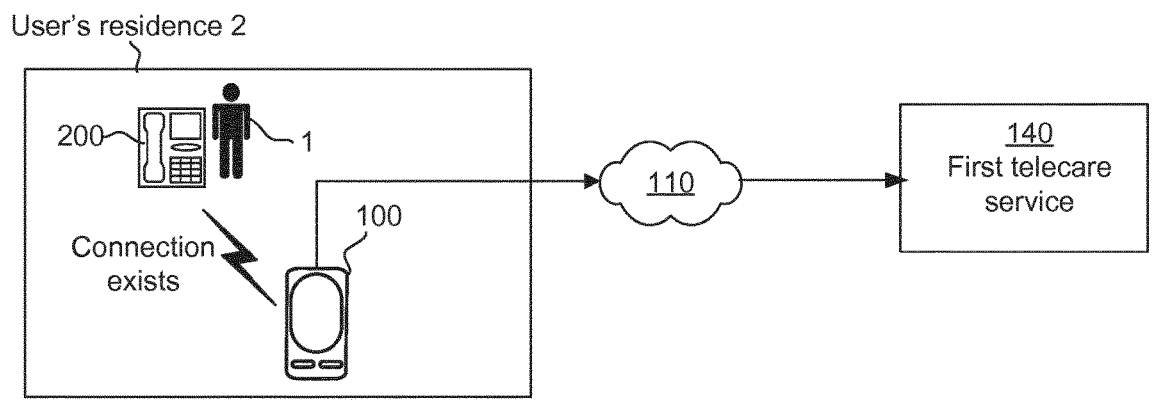

Yet another embodiment is shown in FIG. 4*e*, where the telecare terminal 200, the user 1 and her mobile terminal 100 all are located in the residence 2 of the user. In this example the user 1 presses the assistance button arranged on the telecare terminal 200. Once the dedicated action is detected, the control unit 203 of the telecare terminal 200 will attempt to establish a short-range wireless connection between the telecare terminal 200 and the mobile terminal 100. If the attempt succeeds and a wireless connection is established, the control unit 203 causes transmittal of an assistance request for a first telecare service 140. The generated assistance request is transmitted from the telecare terminal 200 to the mobile terminal 100, thereby enabling the mobile terminal 100 to send the assistance request to the first telecare service 140 through a mobile communication network 110. If the attempt fails and no short-range wireless data communication is established, the control unit 203 causes transmittal of an assistance request for a second telecare service 142. The telecare terminal 200 transmits the generated assistance request to the second telecare service 142.

Figure 4F:
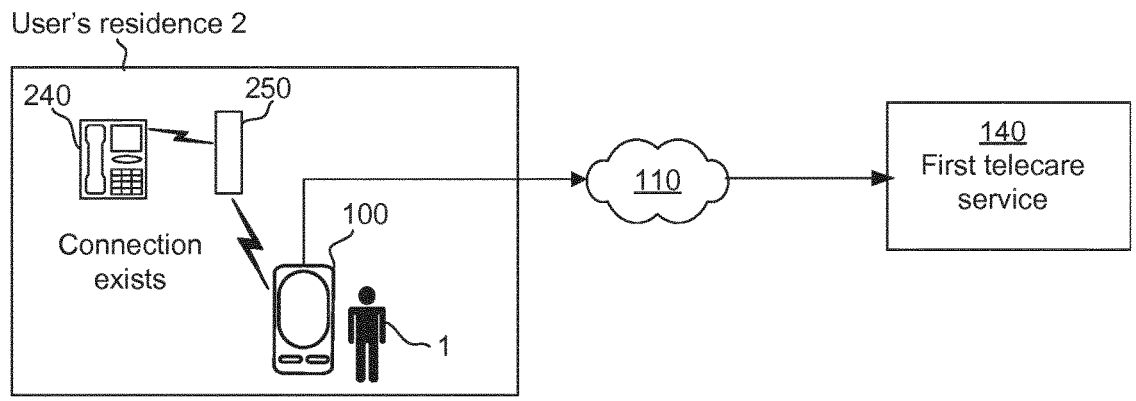

Yet still another embodiment is shown in FIG. 4*f*, where the telecare terminal 200 comprises an assistance unit 240 and a signaling unit 250. Here the assistance unit 240 and the signaling unit 250 are two different devices, both arranged in the residence 2 of the user. Once the user 1 has actuated the dedicated assistance button in the user interface of the mobile terminal 100, the controller 150 of the mobile terminal 100 will attempt to establish an indirect wireless connection between the mobile terminal 100 and the assistance unit 240 via the signaling unit 250. If the attempt is successful and a wireless connection is established, the generated assistance request is sent from the mobile terminal 100 to the first telecare service through a mobile communication network 110. If no short-ranged connection could be established, the mobile terminal 100 will send the assistance request to the second telecare service 142.

Figure 5:
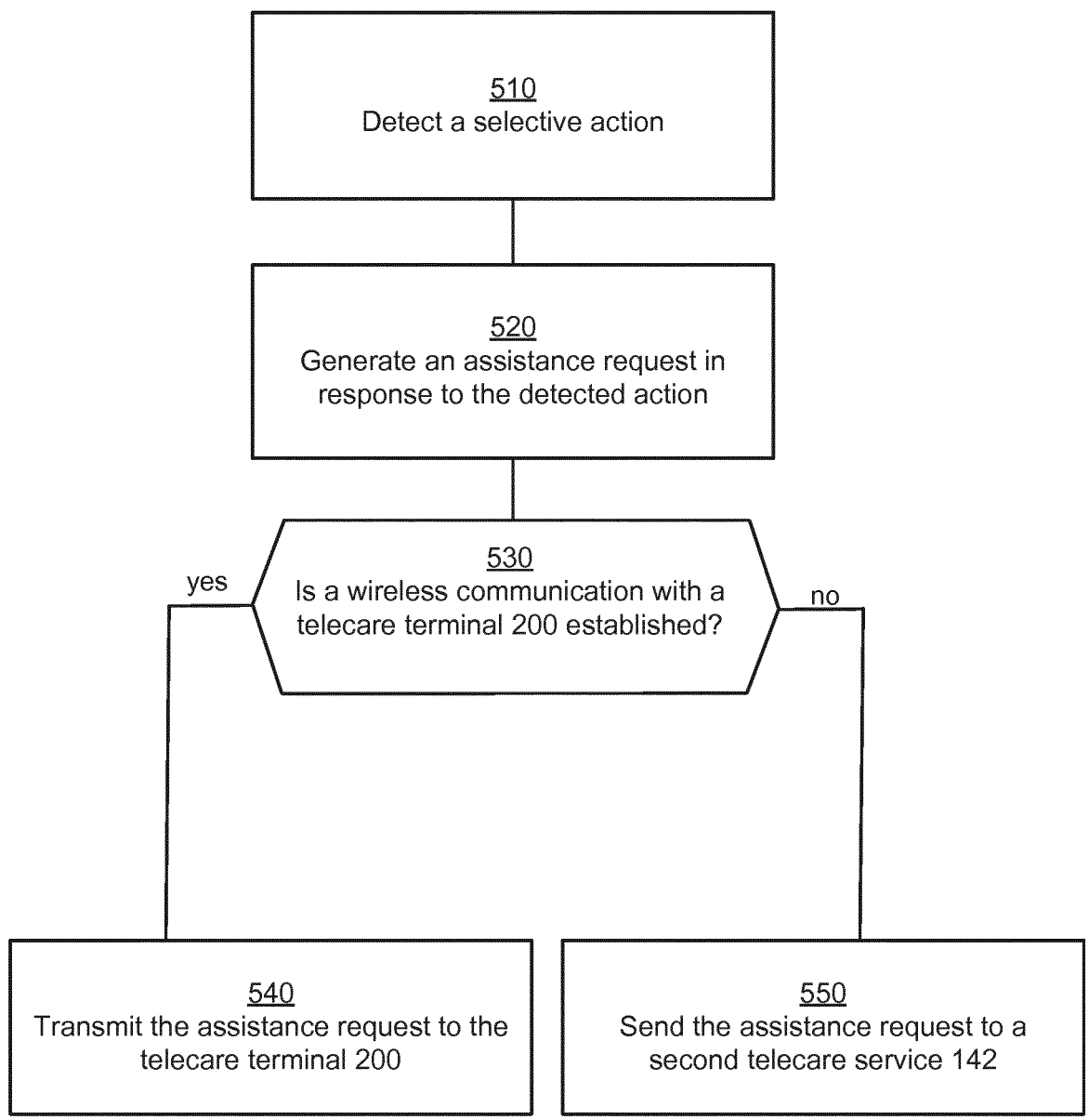
FIG. 5 is a schematic flowchart diagram illustrating a method of a mobile terminal according to an embodiment.

Reference is now made to FIG. 5, which illustrates an embodiment of a method used in the mobile terminal 100 according to the present invention. First, in a step 510, the mobile terminal 100 detects a selective action by the user 1. Then, in response to the selective action an assistance request is generated 520. The mobile terminal 100 attempts to communicate with a telecare terminal 200 using short-range wireless communication, 530. If the communication is successful, the assistance request is transmitted to the telecare terminal 200, step 540, thereby enabling the telecare terminal 200 to send the assistance request to a first telecare service 140 via a communication channel 102. If the communication with the telecare terminal 200 was unsuccessful, the mobile terminal 100 will send the assistance request via a mobile communication network 110 to a second telecare service 142, step 550.

Hence, an assistance request will automatically be transmitted regardless of if a wireless communication is established between the telecare terminal 200 and the mobile terminal 100; the assistance request will however be sent either to the first telecare service 140 or to the second telecare service 142 in response to the outcome of the attempt to establish a wireless communication. The user will thus not have the ability to actively choose between different telecare services 140, since the system described herein makes this determination by itself based on the wireless communication attempt.

This inventive feature provides several safety benefits, since a selective action will always result in that an assistance request is automatically transmitted to one telecare service. For example, if the user were to be able to actively choose between different operators for example presented in a list after a selective action has been made, there would be a risk that the user has become even more in need for assistance during that time, and might for example have passed out. The user would thus be unable to complete the assistance request, which may lead to fatal consequences since no telecare service was contacted.

Additionally, the inventive feature that the system makes the determination of which telecare service 140, 142 to use also has the benefit that the user 1 does not have to understand the difference between the first and the second telecare service 140, 142. Instead, the user 1 can be assured that the correct service provider will be contacted by the system, and he/she does not need to go into details of why and when different telecare services are provided.

Figure 6:
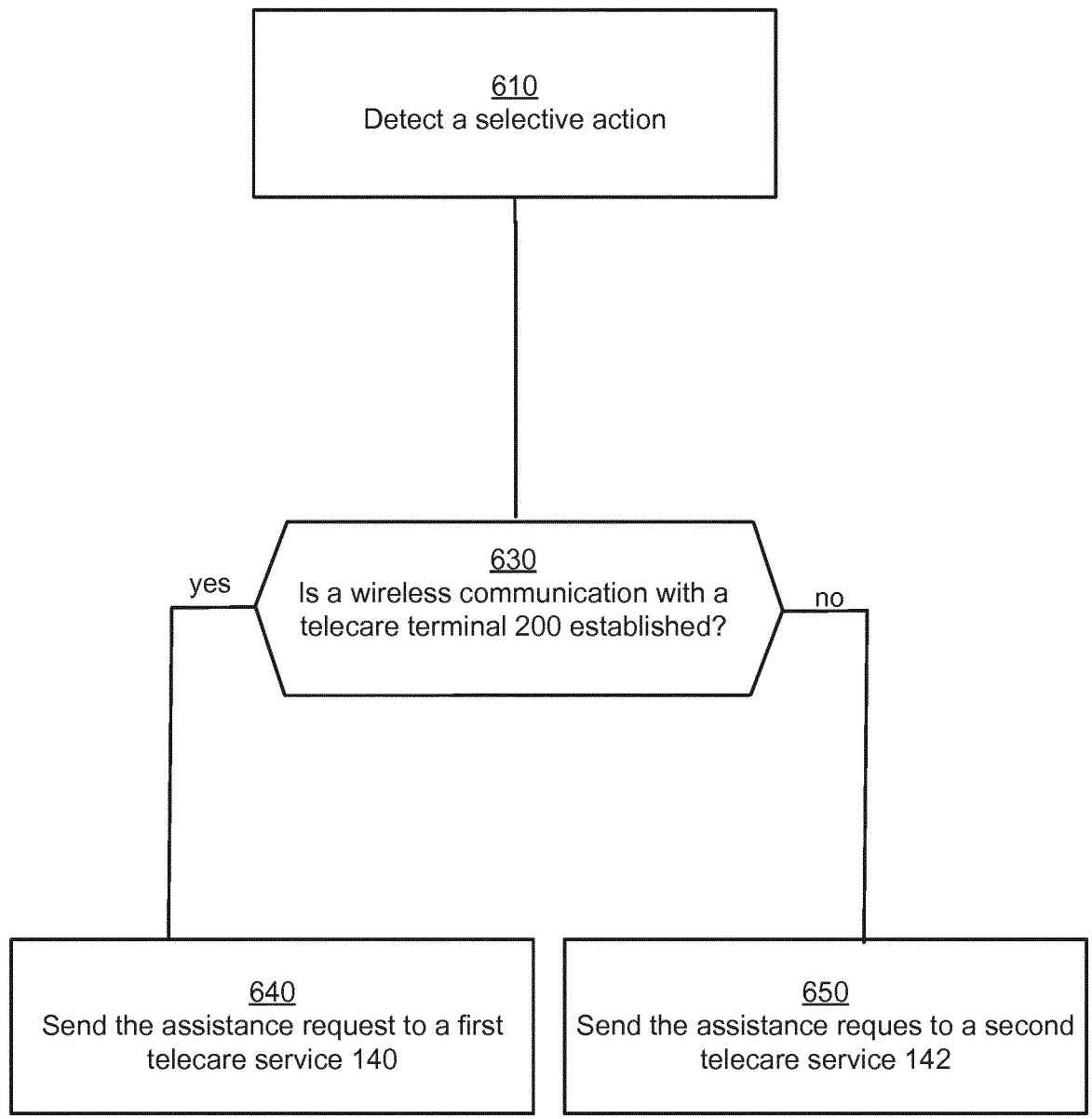
FIG. 6 is a schematic flowchart diagram illustrating a method of a mobile terminal according to an embodiment.

Reference is now made to FIG. 6, which illustrates another embodiment of a method used in the mobile terminal 100 according to the present invention. First, in a step 610, the mobile terminal 100 detects a selective action by the user 1. The mobile terminal 100 attempts to communicate with a telecare terminal 200 using short-range wireless communication, step 630. If the communication was successful, the mobile terminal 100 will send a generated assistance request via a mobile communication network 110 to a first telecare service 140, step 640. If the communication with the telecare terminal 200 was unsuccessful, the mobile terminal 100 will send the assistance request via a mobile communication network 110 to a second telecare service 142, step 650. The assistance request may be generated directly in response to the detection of the selective action by the user 1, or after attempting to establish a short-ranged wireless communication.

Figure 7:
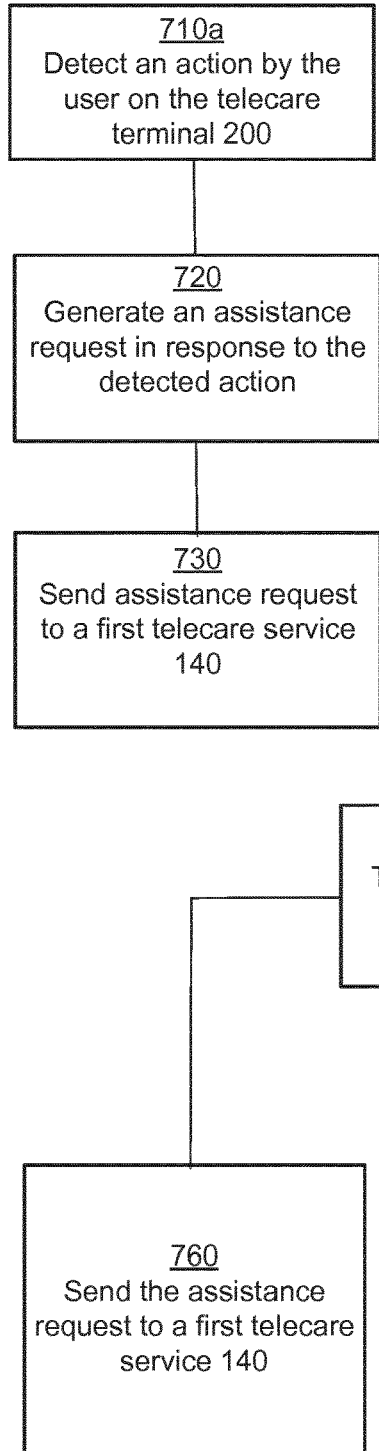
FIG. 7 is a schematic flowchart diagram illustrating a telecare system according to an embodiment.

As is illustrated in FIG. 7, the telecare system operates in the following manner to generate attendance to a first or a second telecare service 140, 142 in response to a selective action by the user 1.

First, in a step 710a and 710b, the mobile terminal 100 or telecare terminal 200 detects a selective action by the user 1.

If the telecare terminal 200 detects the selective action by the user 1, an assistance request is generated in response to the detected action, 720. Then, in a step 730, the assistance request is sent to a first telecare service 140.

If instead the mobile terminal 100 detects the selective action by the user 1, the mobile terminal 100 will attempt to communicate with the telecare terminal 200 using short-range wireless communication, step 740. If the communication between the mobile terminal 100 and the telecare terminal 200 is successful, the mobile terminal 100 will transmit a generated assistance request to the telecare terminal 200, step 750. The telecare terminal 200 will send the assistance request to a first telecare service 140 via a communication channel 102, step 760. If the communication with the telecare terminal 200 was unsuccessful, the mobile terminal 100 will send the assistance request via a mobile communication network 110 to a second telecare service 142, step 770.

The assistance request may be generated directly in response to the detection of the selective action by the user 1, or after attempting to establish a short-ranged communication.

Assistance Request

The assistance request may include information to identify the mobile terminal 100, the telecare terminal 200 and/or the user 1. The assistance request may also include information about date and time, and/or location information retrieved for instance from a satellite (GPS) receiver in the mobile terminal 100 or in the telecare terminal 200. Predefined information regarding the user 1 may also be stored in the memory 205 of the telecare terminal 200 and/or in the memory 160 of the mobile terminal 100 and may be included in the assistance request. Due to the information stored in the assistance request sent out by the mobile terminal 100 and/or the telecare terminal 200 the personnel automatically knows the identity and location of the user.

The assistance request may also include information relating to a user's behavior which may be monitored by the first telecare service 140 and/or by the second telecare service 142. Sensors internal or external to the mobile terminal 100 may be used. For instance, an internal accelerometer may be used to detect a sudden fall of the user 1, or prolonged immobility of the user 1. This may be particularly useful for an individual suffering from illness or physical weakness.

A satellite (GPS) receiver in the mobile terminal 100 may be used for geofencing purposes to detect when the user 1 exits a permitted zone. This may be particularly useful for a disoriented individual suffering for instance from dementia or Alzheimer's disease.

The mobile terminal may receive sensor data or instructions from external equipment via the interfaces 154 or 156. Such equipment may for instance include a video camera, door sensor, smoke detector, etc. The resulting user behavior monitoring data from such internal or external sensors or equipment may be sent as data traffic to the first or second telecare service 140, 142 and/or sent to the telecare terminal 200 possibly after certain preprocessing or decision making already in the mobile terminal 100.

Hence, apart from including the assistance request by the user 1 the request may also include user behavior monitoring data, user medical status data an alarm notification(s).

Telecare Service

One of many benefits from the telecare system which differentiates between a first 140 and a second 142 telecare service as disclosed herein is illustrated with an example. A user may have a subscription with a telecare service, here referred to as the first telecare service 140, which is a service provider paid by the municipality and only covers communication to/from the external device 200. If the user wants to feel safe also outside of her residence and thus benefit from the telecare enabled mobile terminal 200, the user might need another service provider as well, which here is called the second service provider 142. Hence, the first and second telecare service may be different service providers.

In yet another embodiment the first and second telecare service are coupled to the same service providers, but performs different actions depending if the first 140 or the second 142 telecare service is used.

In the case where the first and second telecare service 140, 142 are the same telecare providers, they may have different rates depending on if the assistance request is sent in the vicinity of the residence of the user or if the request is sent for example in another city or country. It is likely that a request for help from a different area than the residence is more costly, since it is outside of the telecare service normal working range.

The first and second telecare services 140, 142 may also differ in that different information from the help request is used depending on the telecare service 140, 142. For example, if a user is outside her residence 2 when in need for assistance, the second telecare service 142 will be activated. It would thus be beneficial for the second telecare service 142 to gain information of the location of the user, for example by using GPS-information stored in the assistance request. However, information concerning data gathered from possible sensors arranged in the residence of the user 2 may not be analyzed due to its low relevance caused by the user not being at home. In another example, if the user is at her residence 2 GPS-information may not be needed when contacting the first telecare service 140, while the data gathered from possible sensors in the residence might be relevant.

When the telecare service 140, 142 receives the assistant request from the mobile terminal 100 or the telecare terminal 200, the telecare service 140, 142 may be configured to transmit an action request to a caregiving entity. This may be done purely automatically or by one or more human operators located at the telecare service 140, 142, using the data stored in the assistant request. The telecare service 140, 142 sends the action request over a communications channel to the caregiving entity. The communications channel may typically involve a PSTN, a mobile telecommunication network or WAN, or combinations thereof.

Typically, the caregiving entity will be a caregiver center which normally provides scheduled caregiving services to the user 1. By issuing the action request to the caregiver center, the telecare service thus urges the caregiver center to attend to the abnormal (i.e. non-scheduled) alarm situation at the caretaker's residence 2. The caregiver center may send an action request confirmation back to the telecare service 140, 142 upon receipt of the action request.

The description above has focused on the situation where an alarm event, and thus the generation of the assistance request, occurs due to a selective action such as a manual actuation by the user 1, e.g. by pressing an alarm button on the telecare terminal 200 or on the mobile terminal 100. Alternatively, the alarm event at the caretaker residence 2 may occur because of automatic detection by a sensor device of an abnormal condition for the caretaker. Such a sensor device may for instance be an accelerometer-based or optical fall sensor detecting a fall accident for the caretaker, a movement sensor detecting a period of immobility for the caretaker 1, or an acoustic sensor detecting a cry for help or a moan from the caretaker 1. As a further alternative, the alarm event at the caretaker residence 2 may occur because of automatic detection by a sensor device of an abnormal condition for the caretaker residence. Such a sensor device may for instance be a smoke, fire or humidity sensor detecting a hazardous situation in the caretaker residence 2, or a burglar alarm sensor detecting a burglar attempt into the caretaker residence 2.

The invention has been described above in detail with reference to embodiments thereof. However, as is readily understood by those skilled in the art, other embodiments are equally possible within the scope of the present invention, as defined by the appended claims.

The invention claimed is:

1. A telecare system, comprising:
    a mobile terminal comprising a controller; and
    a telecare terminal,
    wherein the controller of the mobile terminal is configured to:
    detect a single selective action by a user; and
    in response to the detected single selective action:
        attempt to communicate with the telecare terminal using short-range wireless communication; and
        if the communication was successful, cause transmittal of an assistance request for a first telecare service and if not, cause transmittal of an assistance request for a second telecare service, the assistance request comprising information regarding the request, the information being selected from the group consisting of date, time, and location of the user.

2. The telecare system according to claim 1, wherein the mobile terminal is configured to cause transmittal of the assistance request for the first telecare service by transmitting the assistance request to the telecare terminal, wherein the telecare terminal is configured to receive the assistance request and send said assistance request as data traffic to the first telecare service.

3. The telecare system according to claim 1, wherein the mobile terminal is configured to cause transmittal of the assistance request for the second telecare service by transmitting the assistance request to the second telecare service.

4. The telecare system according to claim 1, wherein the assistance request is generated in response to the detected selective action.

5. The telecare system according to claim 1, wherein the first telecare service and the second telecare service pertain to different service providers.

6. The telecare system according to claim 1, wherein the first telecare service and the second telecare service pertain to the same service provider providing different services.

7. The telecare system according to claim 1, wherein the short-range wireless communication pertains to communication selected from the group consisting of:
    Bluetooth,
    WLAN,
    WiFi,
    NFC,
    RF-ID, and
    IrDA.

8. The telecare system according to claim 1, wherein each of the first telecare service and the second telecare service relates to one or more services selected from the group consisting of:
    a caregiver center;
    a security guard service; and
    an emergency service.

9. The telecare system according to claim 1, wherein the telecare terminal comprises a control unit configured to:
    detect a selective action by a user;
    attempt to communicate with the mobile terminal using short-range wireless communication in response to detected action; and
    if the communication was successful, cause transmittal of an assistance request for a first telecare service and if not, cause transmittal of an assistance request for a second telecare service.

10. The telecare system according to claim 9, wherein the telecare terminal is configured to cause transmittal of the assistance request for the first telecare service by transmitting the assistance request to the mobile terminal, wherein the mobile terminal is configured to receive the assistance request and send said assistance request as data traffic to the first telecare service.

11. The telecare system according to claim 1, wherein the selective action is an actuation of a dedicated assistance button of the mobile terminal.

12. A method in a mobile terminal, wherein the method comprises:
    detecting a single selective action by the user; and
    in response to the detected single selective action:
        attempting to communicate with a telecare terminal using short-range wireless communication; and
        if the communication was successful, causing transmittal of an assistance request for a first telecare service; and if not, causing transmittal of an assistance request for a second telecare service;
        wherein the assistance request comprises information regarding the request, the information being selected from the group consisting of date, time, and location of the user.

13. The method according to claim 12, wherein causing transmittal of the assistance request for the second telecare service is caused by directly transmitting the assistance request to the second telecare service.

14. The method according to claim 12, wherein causing transmittal of the assistance request for the first telecare service is caused by transmitting the assistance request to the telecare terminal, thereby enabling the telecare terminal to send the assistance request as data traffic to the first telecare service.

15. The method according to claim 12, wherein the selective action is an actuation of a dedicated assistance button of the mobile terminal.

16. A mobile terminal comprising a controller, wherein the controller is configured for:
    detecting a single selective action by the user; and
    in response to the detected single selective action:
        attempting to communicate with a telecare terminal using short-range wireless communication; and
        if the communication was successful, causing transmittal of an assistance request for a first telecare service; and if not, causing transmittal of an assistance request for a second telecare service;

wherein the assistance request comprises information regarding the request, the information being selected from the group consisting of date, time, and location of the user.

17. The mobile terminal according to claim 16, wherein the selective action is an actuation of a dedicated assistance button of the mobile terminal.

\* \* \* \* \*

UNITED STATES PATENT AND TRADEMARK OFFICE
CERTIFICATE OF CORRECTION

| | | |
|---|---|---|
| PATENT NO. | : 10,839,673 B2 | Page 1 of 1 |
| APPLICATION NO. | : 16/310127 | |
| DATED | : November 17, 2020 | |
| INVENTOR(S) | : Peter Cullin | |

It is certified that error appears in the above-identified patent and that said Letters Patent is hereby corrected as shown below:

On the Title Page

(73) Assignee: "DORA AB," should read --DORO AB,--

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*